United States Patent
Tallent et al.

(10) Patent No.: US 9,253,259 B2
(45) Date of Patent: ***Feb. 2, 2016

(54) PATIENT SUPPORT, COMMUNICATION, AND COMPUTING APPARATUS

(71) Applicant: Hill-Rom Services, Inc., Batesville, IN (US)

(72) Inventors: Dan R. Tallent, Hope, IN (US); James M. Allen, Batesville, IN (US); Keith A. Huster, Sunman, IN (US); William G. Pittenger, Aurora, IN (US); Irvin J. Vanderpohl, III, Greensburg, IN (US); Christian Saucier, Raleigh, NC (US); John T. Harrington, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 133 days.

This patent is subject to a terminal disclaimer.

(21) Appl. No.: 14/134,145

(22) Filed: Dec. 19, 2013

(65) Prior Publication Data

US 2014/0108611 A1    Apr. 17, 2014

Related U.S. Application Data

(63) Continuation of application No. 13/081,587, filed on Apr. 7, 2011, now Pat. No. 8,618,918.

(60) Provisional application No. 61/322,392, filed on Apr. 9, 2010.

(51) Int. Cl.
*G08B 21/00* (2006.01)
*H04L 29/08* (2006.01)
(Continued)

(52) U.S. Cl.
CPC ............... *H04L 67/12* (2013.01); *A61G 7/018* (2013.01); *G06F 19/327* (2013.01)

(58) Field of Classification Search
CPC ........................................... H04L 67/12
USPC .............. 340/286.06, 286.07, 573.1, 539.12, 340/999; 5/600; 600/300
See application file for complete search history.

(56) References Cited

U.S. PATENT DOCUMENTS

| 3,643,219 A | 2/1972 | Heimann |
| 3,910,659 A | 10/1975 | Peterson |

(Continued)

FOREIGN PATENT DOCUMENTS

| EP | 0168158 | 1/1986 |
| EP | 0 376 066 | 7/1990 |

(Continued)

*Primary Examiner* — Jeffery Hofsass
(74) *Attorney, Agent, or Firm* — Barnes & Thornburg LLP (57) ABSTRACT

A patient support apparatus includes an electronic control system with client browser software running on a general purpose operating system that connects with a remote server via a high speed network connection. The browser and operating system allows the patient support apparatus to access and run programs not designed exclusively for patient support apparatus electronics systems. A general purpose microprocessor along with network converter circuitry allows the patient support to deliver messages in frames having intended recipient addresses. The microprocessor communicates with one or more graphical user interfaces and with a control system that controls actuators of the patient support. The control system may comprise networked nodes, such as CAN nodes for example. Isolation circuitry isolates the patient support from a network of a care facility with which it communicates.

16 Claims, 8 Drawing Sheets

(51) Int. Cl.
*A61G 7/018* (2006.01)
*G06F 19/00* (2011.01)

(56) References Cited

U.S. PATENT DOCUMENTS

| | | |
|---|---|---|
| 3,946,159 A | 3/1976 | Fay |
| 4,356,475 A | 10/1982 | Neumann et al. |
| 4,410,158 A | 10/1983 | Maffei |
| 4,452,499 A | 6/1984 | Verburg |
| 4,489,454 A | 12/1984 | Thompson |
| 4,557,453 A | 12/1985 | McCloskey |
| 4,584,989 A | 4/1986 | Stith |
| 4,607,897 A | 8/1986 | Schwartz |
| 4,640,485 A | 2/1987 | Day et al. |
| 4,687,167 A | 8/1987 | Skalka et al. |
| 4,708,312 A | 11/1987 | Rohr |
| 4,715,385 A | 12/1987 | Cudahy et al. |
| 4,724,555 A | 2/1988 | Poehner et al. |
| 4,738,369 A | 4/1988 | Desjardins |
| 4,747,172 A | 5/1988 | Hohol et al. |
| 4,756,706 A | 7/1988 | Kerns et al. |
| 4,768,241 A | 9/1988 | Beney |
| 4,783,036 A | 11/1988 | Vossoughi |
| 4,835,372 A | 5/1989 | Gombrich et al. |
| 4,836,478 A | 6/1989 | Sweere |
| 4,848,710 A | 7/1989 | Newman |
| 4,852,500 A | 8/1989 | Ryburg et al. |
| 4,857,713 A | 8/1989 | Brown |
| 4,872,679 A | 10/1989 | Bohaski et al. |
| 4,890,856 A | 1/1990 | Mursch et al. |
| 4,934,933 A | 6/1990 | Fuchs |
| 4,945,592 A | 8/1990 | Sims et al. |
| 4,981,139 A | 1/1991 | Pfohl |
| 4,993,683 A | 2/1991 | Kreuzer |
| 5,023,967 A | 6/1991 | Ferrand |
| 5,036,852 A | 8/1991 | Leishman |
| 5,072,906 A | 12/1991 | Foster |
| 5,077,843 A | 1/1992 | Foster et al. |
| 5,108,063 A | 4/1992 | Koerber, Sr. et al. |
| 5,117,521 A | 6/1992 | Foster et al. |
| 5,187,641 A | 2/1993 | Muskatello et al. |
| 5,272,318 A | 12/1993 | Gorman |
| 5,284,255 A | 2/1994 | Foster et al. |
| 5,319,816 A | 6/1994 | Ruehl |
| 5,330,415 A | 7/1994 | Storti et al. |
| 5,335,651 A | 8/1994 | Foster et al. |
| 5,337,845 A | 8/1994 | Foster et al. |
| 5,357,396 A | 10/1994 | Alm |
| 5,362,021 A | 11/1994 | Phillips |
| 5,375,604 A | 12/1994 | Kelly et al. |
| 5,377,371 A | 1/1995 | Foster |
| 5,396,673 A | 3/1995 | Foster |
| 5,398,359 A | 3/1995 | Foster |
| 5,400,991 A | 3/1995 | Werner |
| 5,407,163 A | 4/1995 | Kramer et al. |
| 5,417,222 A | 5/1995 | Dempsey et al. |
| 5,455,975 A | 10/1995 | Foster |
| 5,457,831 A | 10/1995 | Foster et al. |
| 5,473,536 A | 12/1995 | Wimmer |
| 5,473,997 A | 12/1995 | Solomon et al. |
| 5,494,051 A | 2/1996 | Schneider, Sr. |
| 5,497,766 A | 3/1996 | Foster et al. |
| 5,502,480 A | 3/1996 | Kuga et al. |
| 5,513,406 A | 5/1996 | Foster et al. |
| 5,527,289 A | 6/1996 | Foster et al. |
| 5,536,084 A | 7/1996 | Curtis et al. |
| 5,542,138 A | 8/1996 | Williams et al. |
| 5,544,649 A | 8/1996 | David et al. |
| 5,556,065 A | 9/1996 | Wadley |
| 5,561,412 A | 10/1996 | Novak et al. |
| 5,562,091 A | 10/1996 | Foster et al. |
| 5,579,001 A | 11/1996 | Dempsey et al. |
| 5,579,775 A | 12/1996 | Dempsey et al. |
| 5,618,090 A | 4/1997 | Montague et al. |
| 5,623,925 A | 4/1997 | Swenson et al. |
| 5,630,566 A | 5/1997 | Case |
| 5,640,953 A | 6/1997 | Bishop et al. |
| 5,647,491 A | 7/1997 | Foster et al. |
| 5,651,775 A | 7/1997 | Walker et al. |
| 5,664,270 A | 9/1997 | Bell et al. |
| 5,687,717 A | 11/1997 | Halpern et al. |
| 5,699,038 A | 12/1997 | Ulrich et al. |
| 5,712,482 A | 1/1998 | Gaiser et al. |
| 5,715,138 A | 2/1998 | Choi |
| 5,732,401 A | 3/1998 | Conway |
| 5,732,712 A | 3/1998 | Adair |
| 5,738,102 A | 4/1998 | Lemelson |
| 5,738,316 A | 4/1998 | Sweere et al. |
| 5,743,503 A | 4/1998 | Voeller et al. |
| 5,749,374 A | 5/1998 | Schneider, Sr. |
| 5,752,917 A | 5/1998 | Fuchs |
| 5,769,440 A | 6/1998 | Jones |
| 5,771,511 A | 6/1998 | Kummer et al. |
| 5,772,585 A | 6/1998 | Lavin et al. |
| 5,772,599 A | 6/1998 | Nevo et al. |
| 5,788,851 A | 8/1998 | Kenley et al. |
| 5,791,263 A | 8/1998 | Watt et al. |
| 5,799,917 A | 9/1998 | Li |
| 5,820,623 A | 10/1998 | Ng |
| 5,822,544 A | 10/1998 | Chaco et al. |
| 5,826,846 A | 10/1998 | Buccieri et al. |
| 5,831,816 A | 11/1998 | Johns et al. |
| 5,838,223 A | 11/1998 | Gallant et al. |
| 5,842,672 A | 12/1998 | Sweere et al. |
| 5,876,008 A | 3/1999 | Sweere et al. |
| 5,883,370 A | 3/1999 | Walker et al. |
| 5,889,568 A | 3/1999 | Seraphim et al. |
| 5,895,354 A | 4/1999 | Simmons |
| 5,895,571 A | 4/1999 | Utterberg |
| 5,898,961 A | 5/1999 | Ambach et al. |
| 5,903,211 A | 5/1999 | Flego et al. |
| 5,907,291 A | 5/1999 | Chen et al. |
| 5,918,328 A | 7/1999 | Ramsey |
| 5,918,331 A | 7/1999 | Hall et al. |
| 5,918,841 A | 7/1999 | Sweere et al. |
| 5,924,665 A | 7/1999 | Sweere et al. |
| 5,944,659 A | 8/1999 | Flach et al. |
| 5,947,429 A | 9/1999 | Sweere et al. |
| 5,957,838 A | 9/1999 | Rantala |
| 5,960,085 A | 9/1999 | de la Huerga |
| 5,961,448 A | 10/1999 | Swenson et al. |
| 5,966,760 A | 10/1999 | Gallant et al. |
| 5,973,598 A | 10/1999 | Beigel |
| 5,975,081 A | 11/1999 | Hood et al. |
| 5,978,211 A | 11/1999 | Hong |
| 5,991,947 A | 11/1999 | Lavin et al. |
| 5,992,809 A | 11/1999 | Sweere et al. |
| 5,993,006 A | 11/1999 | Takeuchi et al. |
| 5,997,147 A | 12/1999 | Tatoian |
| 6,001,057 A | 12/1999 | Bongiovanni et al. |
| 6,011,701 A | 1/2000 | Kopp et al. |
| 6,012,693 A | 1/2000 | Voeller et al. |
| 6,015,120 A | 1/2000 | Sweere et al. |
| 6,019,332 A | 2/2000 | Sweere et al. |
| 6,027,247 A | 2/2000 | Tachi et al. |
| 6,061,104 A | 5/2000 | Evanicky et al. |
| 6,064,373 A | 5/2000 | Ditzik |
| 6,065,732 A | 5/2000 | Cho |
| 6,073,285 A | 6/2000 | Ambach et al. |
| 6,089,518 A | 7/2000 | Nilsson |
| 6,102,476 A | 8/2000 | May et al. |
| 6,102,855 A | 8/2000 | Kehr et al. |
| 6,104,443 A | 8/2000 | Adcock et al. |
| 6,112,182 A | 8/2000 | Akers et al. |
| 6,125,350 A | 9/2000 | Dirbas |
| 6,134,103 A | 10/2000 | Ghanma |
| 6,143,181 A | 11/2000 | Falkvall et al. |
| 6,144,848 A | 11/2000 | Walsh et al. |
| 6,146,523 A | 11/2000 | Kenley et al. |
| 6,150,942 A | 11/2000 | O'Brien |
| RE36,978 E | 12/2000 | Moscovitch |
| 6,155,603 A | 12/2000 | Fox |
| 6,155,975 A | 12/2000 | Urich et al. |
| 6,168,250 B1 | 1/2001 | Rogov |

(56) References Cited

U.S. PATENT DOCUMENTS

| | | |
|---|---|---|
| 6,170,102 B1 | 1/2001 | Kreuzer |
| 6,175,779 B1 | 1/2001 | Barrett |
| 6,175,977 B1 | 1/2001 | Schumacher et al. |
| 6,176,456 B1 | 1/2001 | Wisniewski |
| 6,179,260 B1 | 1/2001 | Ohanian |
| 6,183,417 B1 | 2/2001 | Geheb et al. |
| 6,189,842 B1 | 2/2001 | Bergeron Gull et al. |
| 6,202,360 B1 | 3/2001 | Rattner et al. |
| 6,202,923 B1 | 3/2001 | Boyer et al. |
| 6,205,601 B1 | 3/2001 | Nessmann et al. |
| 6,219,587 B1 | 4/2001 | Ahlin et al. |
| 6,234,172 B1 | 5/2001 | Ausbourne et al. |
| 6,246,573 B1 | 6/2001 | Khan et al. |
| 6,260,761 B1 | 7/2001 | Peoples, Jr. |
| 6,352,504 B1 | 3/2002 | Ise et al. |
| 6,493,568 B1 | 12/2002 | Bell et al. |
| 6,510,049 B2 | 1/2003 | Rosen |
| 6,611,979 B2 | 9/2003 | Welling et al. |
| 6,616,606 B1 | 9/2003 | Petersen et al. |
| 6,658,680 B2 | 12/2003 | Osborne et al. |
| 7,032,522 B2 | 4/2006 | George et al. |
| 7,154,397 B2 | 12/2006 | Zerhusen et al. |
| 7,237,287 B2 | 7/2007 | Weismiller et al. |
| 7,444,704 B2 | 11/2008 | Phillips et al. |
| 7,679,520 B2 | 3/2010 | Zerhusen et al. |
| 7,911,349 B2 | 3/2011 | Zerhusen et al. |
| 7,962,981 B2 | 6/2011 | Lemire et al. |
| 7,979,169 B2 | 7/2011 | Rawls-Meehan |
| 8,618,918 B2 | 12/2013 | Tallent et al. |
| 2002/0014951 A1 | 2/2002 | Kramer et al. |
| 2002/0044059 A1 | 4/2002 | Reeder et al. |
| 2002/0053086 A1 | 5/2002 | Vanderpohl et al. |
| 2002/0152211 A1 | 10/2002 | Jam |
| 2002/0196150 A1 | 12/2002 | Wildman |
| 2003/0052787 A1 | 3/2003 | Zerhusen et al. |
| 2006/0180054 A1 | 8/2006 | George et al. |
| 2007/0120689 A1 | 5/2007 | Zerhusen et al. |
| 2007/0157385 A1* | 7/2007 | Lemire et al. .............. 5/600 |
| 2010/0132122 A1* | 6/2010 | Hollingshead ............ 5/658 |
| 2010/0154124 A1 | 6/2010 | Zerhusen et al. |
| 2011/0247139 A1 | 10/2011 | Tallent et al. |

FOREIGN PATENT DOCUMENTS

| | | |
|---|---|---|
| GB | 2 218 149 | 8/1989 |
| GB | 2 333 391 | 7/1999 |
| WO | WO 94/13198 | 6/1994 |
| WO | WO 98/02107 | 1/1998 |
| WO | WO 98/29775 | 1/1998 |
| WO | WO 99/52487 | 10/1999 |
| WO | WO 01/57610 | 8/2001 |

\* cited by examiner

PATIENT SUPPORT, COMMUNICATION, AND COMPUTING APPARATUS

CROSS REFERENCE TO RELATED APPLICATIONS

This application is a continuation of U.S. application Ser. No. 13/081,587, filed Apr. 7, 2011, issued as U.S. Pat. No. 8,618,918, which claims the benefit, under 35 U.S.C. §119(e), of U.S. Provisional Patent Application No. 61/322,392, filed Apr. 9, 2010, and each of which is hereby incorporated by reference herein.

BACKGROUND

The present disclosure relates to patient support apparatuses, such as beds, mattresses, stretchers and the like. More particularly, the present disclosure relates to patient support, communication, and computing apparatuses.

Patient support apparatuses such as hospital beds conventionally have features adapted to provide comfort to the patient, as well as to assist the caregiver in positioning and transporting the patient. For example, such beds can include articulating sections to allow the patient to be placed in a variety of positions, for comfort of the patient and to assist the caregiver in caring for the patient. Such beds might also include electronic displays to indicate the status of the various features of the bed, such as the brake status, the siderail position, and the bed height. Additionally, such beds can allow for communications with remote caregivers.

While such systems can be very useful in assisting caregivers and providing improved safety and comfort to patients, their capabilities heretofore have been limited in some ways. In particular, there is still room for improvement in the capabilities of such systems and the value they provide to hospital workers and hospital administrators. Thus, a need persists for further contributions in this area of technology.

SUMMARY

A patient support apparatus according to this disclosure includes one or more of the features recited in the appended claims and/or one or more of the following features, which alone or in any combination may comprise patentable subject matter:

According to this disclosure, a person support apparatus may comprise an upper surface configured to support a person, a movable actuator configured to impart movement to at least a portion of the upper surface, and an electronics system connected to the person support apparatus and configured to control the movable actuator. The electronics system may comprise a processor, a memory, a user interface configured to display information as directed by the processor, a network connector configured to connect to a hospital network via hardwired connection, and a network interface. The network interface may be configured to receive data at a data transfer rate of greater than 1 Mb per second, at least part of the time, and may be configured to allow for data communication with a hospital network via the network connector. The electronics system may further comprise a general purpose operating system executable by the processor, and the general purpose operating system may be configured to run, without modification, a plurality of computer software applications not designed for person support apparatuses. The system may also comprise browser software executable by the processor and configured to allow the electronics to act as a client computer by sending a request to a remote server to perform a task, receiving data defining a screen to be displayed on the user interface in response to the request, receiving input from a user at a portion of the screen, and sending the input to the remote server.

Additionally, the electronics system may comprise control software configured to control the movable actuator through at least one input from a user, and an electrical isolator configured to provide electrical isolation of the network connector from at least a portion of the electronics system. In some embodiments, the electrical isolator may provide at least 2.5 mm creepage distance and at least 2.0 mm air clearance, such as at least 4.0 mm creepage and 2.5 mm air clearance for example. In some embodiments, the electronics system may be configured to receive an identification of the room in which the patient support is located and to send the identification via the network connector. In some embodiments, the electronics system may be configured to cause a location identification signal to be communicated to the remote server, such that the remote server can associate the data from the electronics system to a physical location in a hospital.

According to this disclosure, the electronics system may comprise a processor, memory, a graphical user interface configured to display information as directed by the processor, and a high speed network interface. The system may further comprise a general purpose operating system configured to receive data from a remote server application over the high speed network interface and to operate the graphical user interface as a client computer of a remote server computer. The electronics system may be configured to control the actuator to move the surface. In some embodiments, an isolator is provided which isolates the network interface, and the isolator may have at least 2.5 mm creepage distance and at least 2.0 mm air clearance, such as at least 4.0 mm creepage and 2.5 mm air clearance, for example. In some embodiments, the network interface may have a data transfer rate of at least 1 Megabits per second.

In some embodiments, the electronics system may comprise a processor having a speed of at least about 300 MHz, a volatile memory having a size of at least about 128 Megabytes, a nonvolatile memory having a size of at least about 64 Megabytes, a graphical user interface configured to display information as directed by the processor, and a high speed network interface. The electronics system may further comprise a general purpose operating system capable of being installed on multiple disparate devices and configured to receive data from a remote server application over the high speed network interface. The high speed network interface may have a data communication speed of at least 1 Megabit per second at least part of the time. The electronics system may be configured to control the actuator to move the surface. In some embodiments, the operating system may be configured to allow the person support apparatus to share computing resources with a remote server computer. In some embodiments, the processor may include at least two of an integrated Ethernet interface, an integrated CAN interface, an integrated image processing unit, and a USB interface. In some embodiments, the apparatus may comprise at least one USB port provided on the patient support apparatus and connected with the electronics system.

In some embodiments, the electronics system may comprise a processor, a memory, a user interface configured to display information as directed by the processor, a network interface, software executable by the processor and configured to allow the electronics to act as a client computer by generating requests for a server to perform a task, to display a screen related to the task on the user interface, to receive input related to the task from a user viewing the screen, and to send the input to the server.

According to this disclosure, a healthcare computer network may be provided and may comprise a first computer configured to operate as at least one of a network server and a network client, a person support apparatus, and a second computer coupled to the person support apparatus and including a network interface. The second computer may be configured to communicate with the first computer via the network interface and to operate as at least one of a network client and a network server.

Also according to this disclosure, a healthcare computer system may comprise a person support apparatus having an upper surface configured to support a person, a movable actuator configured to impart movement to at least a portion of the upper surface, and an electronics system connected to the person support apparatus and configured to control the movable actuator. The electronics system may comprise a processor, a memory, a user interface configured to display information as directed by the processor, a network interface, control software, and a general purpose operating system. The network interface may be configured to communicate data with a hospital network at a data transfer rate of greater than 1 Mb per second, at least part of the time. The general purpose operating system may be executable by the processor and may be configured to run, without modification, a plurality of computer software applications not designed for person support apparatuses. The control software may be configured to control the movable actuator through at least one input from a user. The healthcare computer system may comprise a location identification circuit configured to provide a location of the patient support. In some embodiments, the electronics system may be configured to transfer the location to a remote computer. In some embodiments, the location and data from electronics system may be associated at the remote computer.

These and other features, alone or in combination with any other feature(s), such as those described herein and/or those listed in the claims, may comprise patentable subject matter. Such features and principles of the disclosure will become apparent to those skilled in the art upon consideration of the following detailed description of various examples and embodiments illustrating the best mode of carrying out the features and principles as presently perceived.

BRIEF DESCRIPTION OF THE DRAWINGS

The detailed description particularly refers to the accompanying figures, in which.

DETAILED DESCRIPTION

In one illustrative embodiment, a patient support apparatus is provided that includes an electronic control system with client browser software running on a general purpose operating system that connects with a remote server via a high speed network connection. The browser and operating system allow the patient support apparatus to access and run programs not designed exclusively for patient support apparatus electronics systems. A general purpose microprocessor along with network converter circuitry allows the patient support to deliver messages in frames having intended recipient addresses. The microprocessor communicates with one or more graphical user interfaces and with a control system that controls actuators of the patient support apparatus. The control system may comprise networked nodes, such as CAN (controller area network), LON (local operating network), USB (universal serial bus), or Ethernet nodes, for example. Isolation circuitry isolates the patient support from a network of a care facility with which it communicates. A connector for a personal storage device is provided on the patient support, such as at a siderail or endboard, for downloading or uploading data and files. Other embodiments incorporating one or more of these features are possible.

Figure 1:
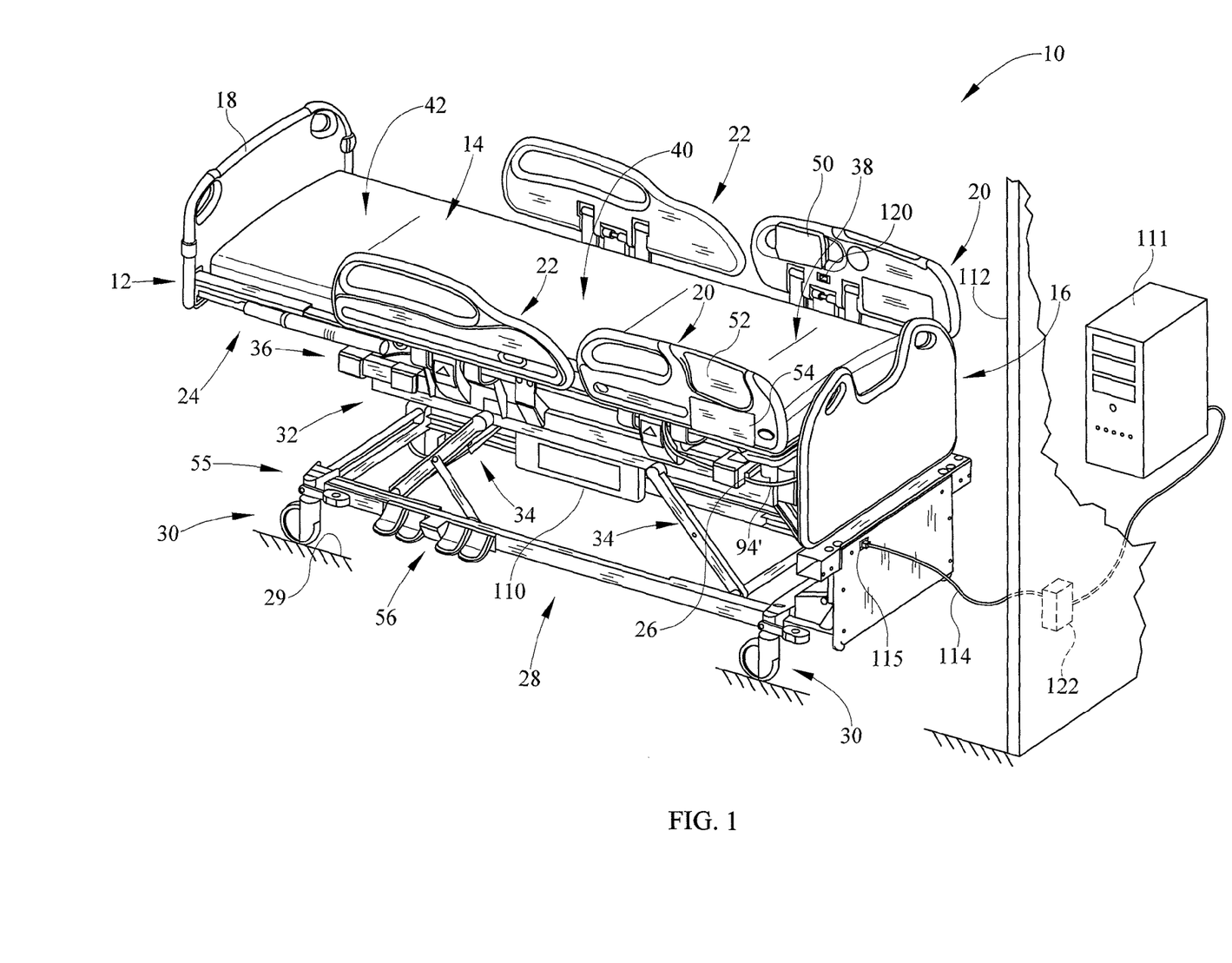
FIG. 1 is a perspective, partial schematic view of an embodiment of a patient support apparatus, configured in accordance with one or more principles of the present disclosure.
Figure 2:
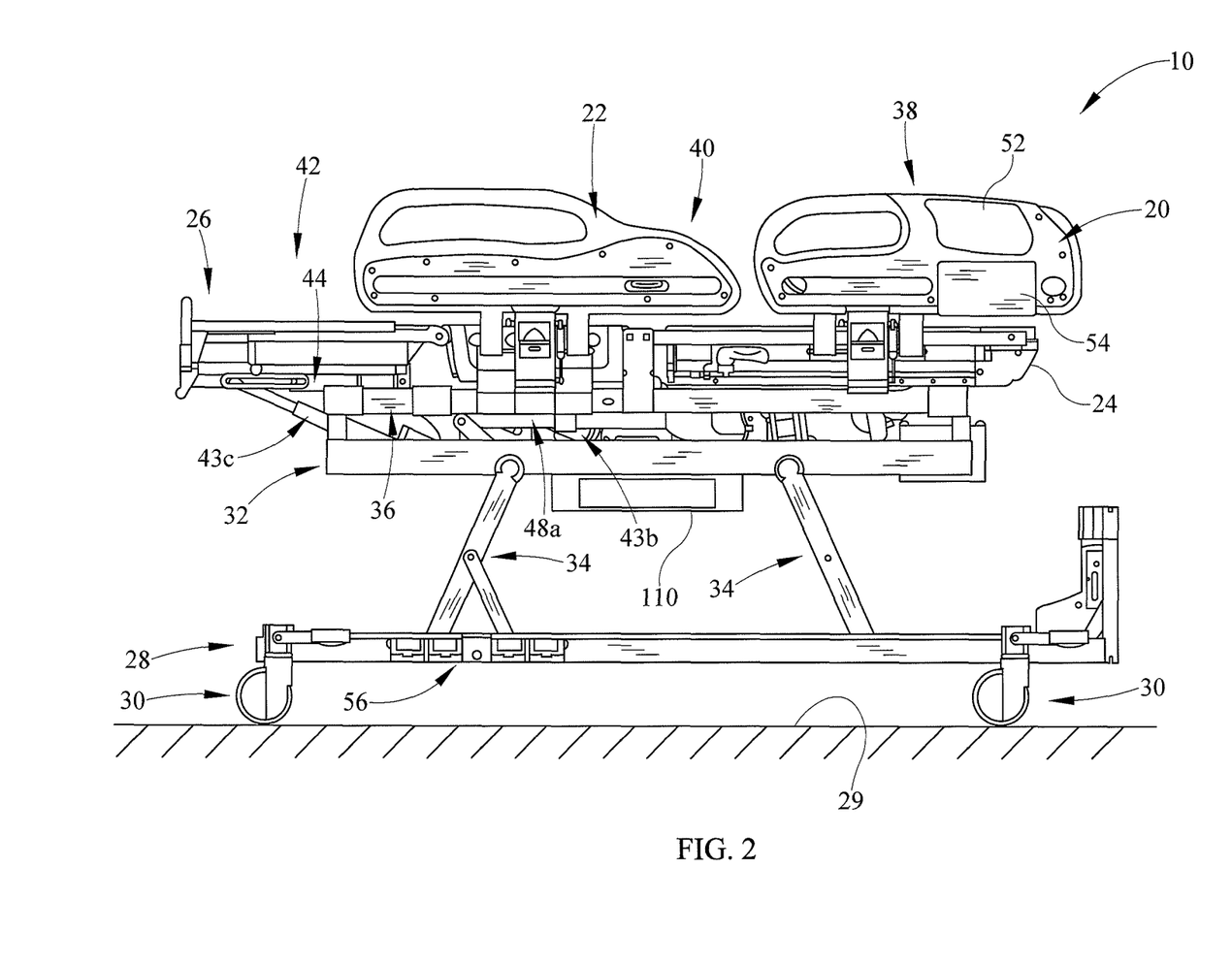
FIG. 2 is a side elevation view of the patient support of FIG. 1, showing the deck support in an upper position and the deck sections in a linear relationship or bed configuration.
Figure 3:
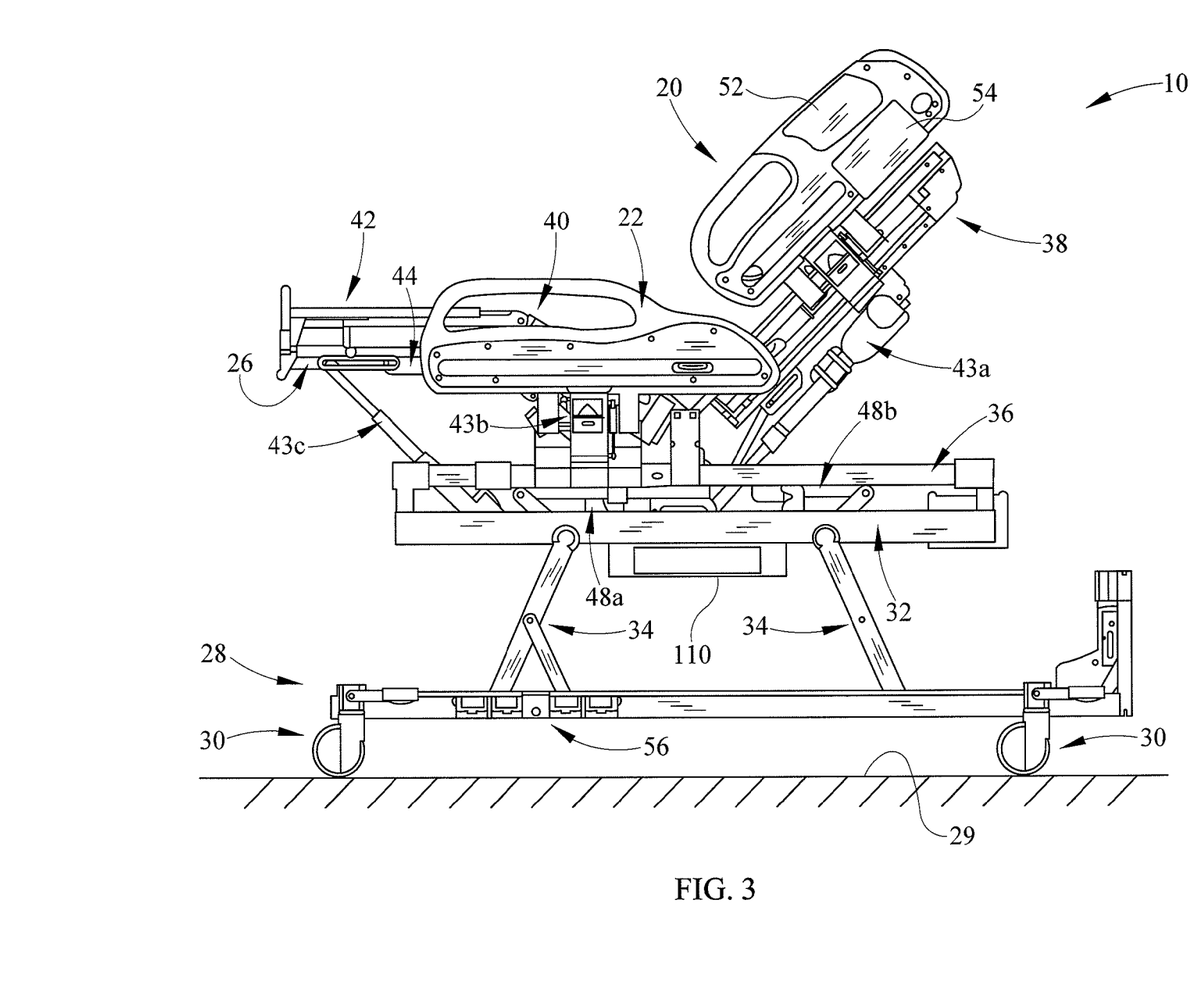
FIG. 3 is a side elevation view of the patient support of FIG. 1, showing the deck support in an upper position, a head section of the deck elevated by a head section actuator and a seat section of the deck elevated by a seat section actuator.

A patient support 10 according to an illustrative embodiment of the present invention is shown in FIGS. 1-3. Patient support 10 includes a frame 12, a mattress 14 supported by frame 12, a headboard 16, a footboard 18, a pair of head end siderails 20, and a pair of foot end siderails 22. Frame 12 includes a deck support 24 and a deck 26 supporting mattress 14. Deck support 24 includes a base frame 28 supported on the floor 29 by a plurality of caster wheels 30, an intermediate frame 32, first and second pairs of lift arms 34 configured to raise and lower intermediate frame 32 relative to base frame 28, and a weigh frame 36 supported by intermediate frame 32, so as to allow the patient support 10 to be raised and lowered to any position between a high and a low position.

Deck 26 is supported by weigh frame 36 and is configured to articulate between a plurality of positions. More particularly, deck 26 illustratively includes a head section 38 pivotably coupled to weigh frame 32, a seat section 40 pivotably coupled to weigh frame 32, and an adjustable length leg section 42 pivotably coupled to seat section 40. The deck 26 is illustrated in a first configuration in FIGS. 1 and 2, while the deck 26 is illustrated in a second configuration in FIG. 3. In the first configuration of FIGS. 1 and 2, head section 38, seat section 40, and leg section 42 are in a substantially linear or planar relationship. In the second configuration of FIG. 3, head section 38 of deck 26 is elevated by a head section actuator 43a and seat section 40 of deck 26 is elevated by a seat section actuator 43b. A leg section actuator 43c is likewise configured to move leg section 42 relative to seat section 40. An extension actuator 44 is configured to extend and retract the adjustable length leg section 42.

Additional details of illustrative deck support 24 and deck 26 can be found in U.S. Pat. No. 6,658,680, issued Dec. 9, 2003 and U.S. Pat. No. 6,611,979, issued Sep. 2, 2003, both of which are assigned to the assignee of the present invention and the disclosures of which are expressly incorporated herein by reference.

Head end siderails 20 are coupled to head section 38 of deck 26 and can be moved relative to mattress 14 between raised and lowered positions. Foot end siderails 22 are coupled to weigh frame 32 and can also be moved relative to mattress 14 between raised and lowered positions.

The illustrative embodiment of FIG. 1 further includes an electronics system 110 located primarily beneath the deck 26 of the bed 10. The electronics system 110 of this embodiment controls client browser software, shown on display 50. The browser software, in conjunction with electronics system hardware, allows the bed 10 to serve as a client device to a remote server 111, shown outside of wall 112. Accordingly, the electronics system sends requests to server 111 for a task to be performed, via network connection 114 and network connector 115 (e.g., a jack). The server then runs an application in response to the request, and return data and/or images to be displayed back to the electronics system 110. The system 110 then displays the data and/or images as screens or pages on a client browser application displayed on user interface 50 located in or on the siderail 20. The server 111 runs a variety of off-the-shelf software applications, such as hospital information system applications and/or home computing applications, not specifically designed for beds or patient supports. As described in more detail below, the electronics system 110 of the bed 10 is configured with hardware and software to allow such applications to be displayed and controlled by a user (caregiver and/or patient) of the bed 10.

The electronics system 110 of the bed 10 also controls bed control software, user interfaces for which are shown on second display 52. The bed control software allows the user to move various portions of the bed. For example, as shown in FIG. 3, the foot, thigh, seat, and head sections of deck 26 can be moved relative to the base frame 28, such as via electric linear actuators 43a, 43b, and 43d. The user can provide inputs to the bed control software via the display 52, to cause movement of the bed actuators, and/or to set alarm levels at which the bed will sound and/or show an alarm state. The display can be a touchscreen, for example, or can have associated buttons to enable the inputs to be made to the control software.

The electronics system 110 includes isolation circuitry to isolate the server 111 and connection 114 and connector 115 from the remainder of the electronics system and associated bed components. Such circuitry is operated using inductive, capacitive, magnetic, and/or optical isolation components, for example. As one example, the isolator comprises an isolator that isolates an Ethernet signal, or a digital isolator that isolates a processor signal from the signal provided at the connector 115.

As further shown in FIG. 1, the siderail 20 includes a USB port 120 that allows a user to connect to the electronics system 110. For example, the user could save data via the universal serial bus (USB) port 120, as controlled by the browser on graphical user interface 50. Such data could be related to the bed settings or the patient. Alternatively, the user can load software onto the electronics system 110 via the USB port 120, such as for example to update the control software, to load user applications, transfer files, or to trouble shoot the electronics 110. As another example, the user could load data from the USB port 120 into the electronics system 110, indicative of the desired settings of the bed 10 (head deck angle, bed height, desired therapy) and/or other hospital preferences regarding the room, food, or facilities. Although a USB port is shown and described, various types of user/programmer data ports (serial, parallel, firewire, RS standard ports, IEEE standard ports, USB, etc) could be provided on the bed 10, and at various locations (frame, deck, headboard, footboard, etc). For example, the port could be on another siderail 22 or 18, or on the frame 28 or 32, or on an electronics control box for the system 110.

In this example, a room identification transmitter 122 is provided in or on wall 112 to provide an indication of which room the bed is in. This can be achieved by sending a room identification signal to the bed which then communicates that signal on to the network server, or by sending the bed data and the room identification signal along the same channel, grouped together, or otherwise with some association that allows the server 111 to match the bed and bed data to the appropriate room. Therefore, such association can allow the server 111 to associate data related to the bed 10 or the room with the patient known to be assigned to that room. In this example, the room identifier signal is sent from the identification transmitter 122 over the cable 114, through the connector 115 to the electronics system 110. The system 110 then relays the room identifier back through the cable 114 along with the network signal that goes back to the server 111. In this manner, the bed 10 tells the network server 111 which room it is in, so that appropriate associations of bed data to patient can be made and so appropriate alarming can be set. For example, knowing which room (or part of the room) the bed 10 is in, and which patient is supposed to be in that room (or part of the room), the server can set certain bed alarm levels based on whether the patient is a falls risk. A falls risk patient might require all siderails up, all brakes set, bed in low height, and patient position monitor set. If any of these conditions becomes untrue, then the server 111 can generate an alarm signal sent back through the network connection 114 to the bed, to sound an alarm at the bed 10 and/or at a nurses station or audio station connected to the network. As another example, if it is known that the patient in that room is at risk for lung complications, the server 111 can initiate or request percussion, vibration, or rotation therapy via the browser on display 50.

Server 111 can also provide other services for the users of the bed 10, such as network access to a variety of software applications providing entertainment, data, information, multimedia, audio, video, and communications services on client display 50. For example, the user might access audio files such as MP3 music files, video files such as MPEG movie files, information files such as patient care instructions, e-communication services such as email, audio communications such as voice over internet communications, and/or other network services provided by intranet, extranet, LAN, WAN, or other network hardware. Such access may be software restricted, such as by a access control application (e.g., a filtering program) that limits access to certain sites or site types, and to certain files, file sizes, or file types. For instance, a preapproved list of allowed network or Internet links can be provided by the access control application, and access can be provided only through predetermined icons or links.

As previously described and as shown in FIG. 1, deck support 24 includes a base frame 28 supported on the floor 29 by a plurality of caster wheels or caster devices 30, an intermediate frame 32, first and second pairs of lift arms 34 configured to raise and lower intermediate frame 32 relative to base frame 28, and a weigh frame 36 supported by intermediate frame 32. Linear actuators 48a and 48b, shown in FIG.

3, provide power to actuate lift arms 34 and in turn to raise and lower intermediate frame 32 relative to base frame 28.

Siderails 20, 22 can include a series of buttons for controlling the various functions of hospital bed 10 via the control program, in conjunction with or as alternatives to graphical user interface 52. Deck 26 can include head, back, seat, and foot portions or sections that can be tilted relative to intermediate frame 32 and several mechanisms configured to adjust the angular position of these deck sections. In this example, leg section of deck 26 is extendable and can be raised while the thigh section pivots relative the seat. Additionally, head section of deck 26 can also be tilted relative to intermediate frame 32. The lift arms 34 raise and lower the deck 26 relative to the base frame 28.

Figure 4:
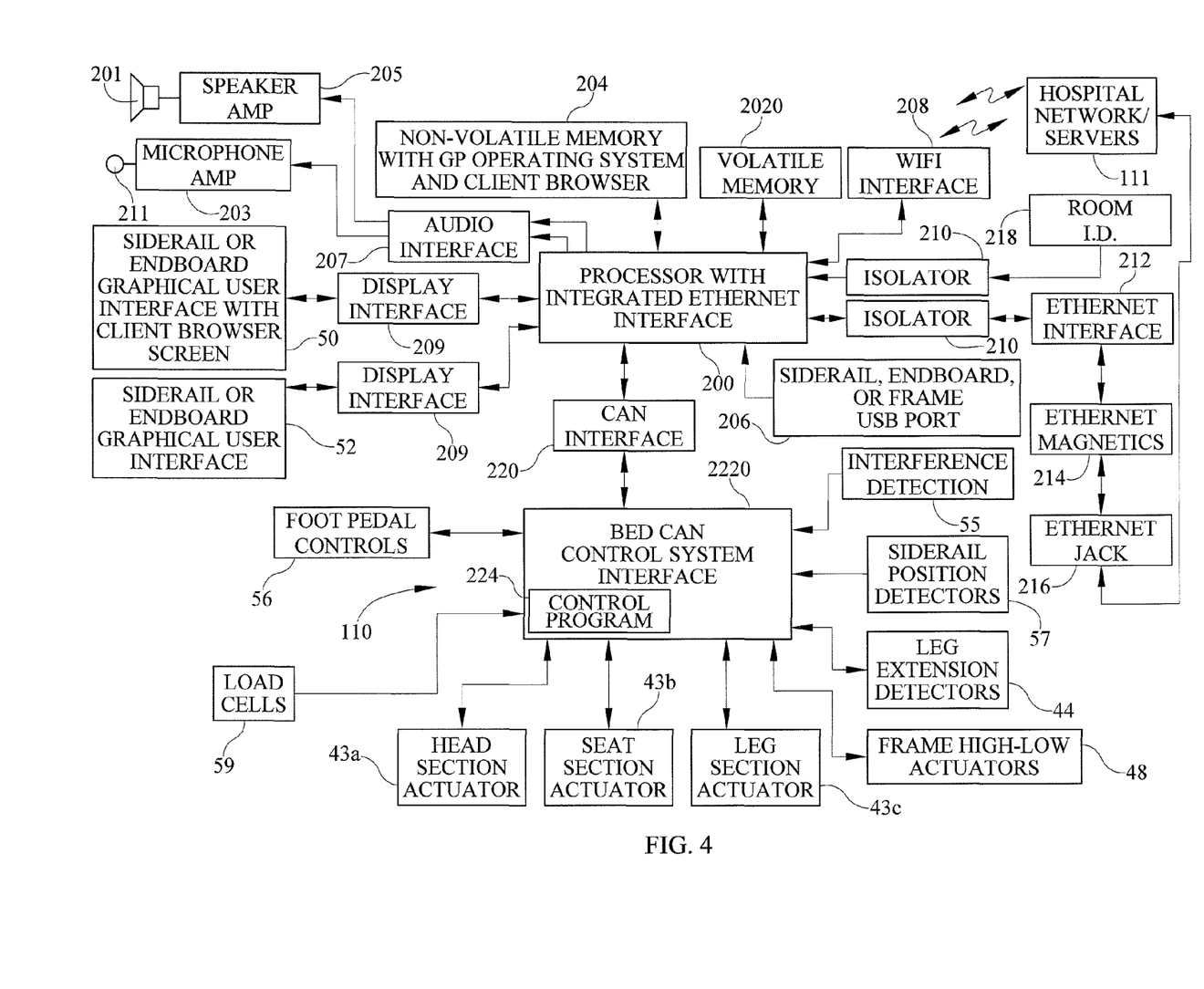
FIG. 4 is a block diagram of one embodiment of an electronic system for a patient support, configured in accordance with one or more principles of the present disclosure.

FIG. 4 is a block diagram of an electronic control system 110 that provides control of various functions of a patient support, and which could be used for the electronics control system 110 of FIGS. 1-3. Control system 110 operates and monitors linear actuator 44 to extend and retract adjustable length leg section 42, and linear actuators 48 to move intermediate frame 32 relative to base frame 28. Control system 110 further operates and monitors linear actuators 43a, 43b and 43c to move head section 38 relative to weigh frame 36, seat section 40 relative to weigh frame 36, and leg section 42 relative to seat section 40, respectively.

Control system 110 includes a plurality of input devices including graphical user interfaces 50, 52, and foot pedal controls 56 coupled to base frame 28. Control system 110 also includes an interference detection device 55, such as optical or switch based obstacle detection systems, coupled to base frame 28 to detect possible clearance issues between intermediate frame 32 and base frame 28. Control system 110 further illustratively includes a plurality of actuator position detectors or motor sensors (not shown) provided with each of the plurality of actuators 43a, 43b, 43c, 44, 48. A plurality of load cells 59 are provided between weigh frame 36 and intermediate frame 32 to provide signals that indicate the weight supported by intermediate frame 32. Control system 110 uses these signals to determine the weight of a patient positioned on mattress 14. Additionally, control system 110 includes a plurality of siderail position detectors or sensors 57 configured to provide signals indicative of the vertical position of siderails 20, 22.

In this illustrative embodiment, a controller area network system 2220 executes a control program 224 to control the various actuators and components. Such a system can include one or more controller area network (CAN) controller nodes to control the various actuators. If multiple controller nodes are utilized, the nodes can communicate with one another via serial bus connections. The control program can comprise control software or other logic that indicates desired control logic for the bed, such as which actuators to operate in response to which user inputs, what sensor to display on the user interfaces 50, 52 at what times, how to convert data from load cells 59 into patient weight, and what alarms to sound via speaker 201 and/or user interfaces 50, 52 in response to which sensor inputs (siderails up/down, brakes set/notset, bed low/notlow, patient position). The control program 224 could be stored in this example in the electronic system of the bed (for example in electronics system 110 of the example bed of FIG. 1). In one embodiment the electronics system 2220 comprises two control boards, one of which receives inputs from user input devices and which stores the control program 224, and the other of which receives inputs from the user input control board and translates the inputs into corresponding appropriate signals that can be used by the actuators.

A microprocessor 200 controls operation of the displays 50 and 52, as well as communicates with the bed control system 2220 via a CAN interface circuit 220. The CAN interface 220 allows the microprocessor 200 to deliver input commands to the control system 2220 to move an actuator or set an alarm signal. The interface 220 likewise allows the CAN control system 2220 to deliver actuator status information and other information to the microprocessor 200, which can then be displayed on displays 50 and 52 as desired. The CAN interface 220 comprises appropriate circuitry or integrated circuitry that allows the microprocessor 200 to communicate with control system 2220. CAN interface 220 can comprise for example, a high speed CAN transceiver.

The microprocessor 200 communicates with hospital server 111 and further is configured to allow the system 110 to act as a client to the server 111. Microprocessor 200 accesses nonvolatile memory 204 in which is stored client browser software and a general purpose operating system. The general purpose operating system can comprise an operating system available for a variety of applications unrelated to patient support apparatus, such as for home computing applications, and/or other industrial applications. For example, the Windows CEO operating system or the Linux operating system can be utilized. Such operating systems can include a plurality of drivers for operating a variety of peripheral equipment, such as storage devices, printers, scanners, or other equipment. Such operating systems can also be capable of loading and running a variety of standard pre-existing applications that might not be designed for patient support apparatus. The client browser can comprise Internet Explorer®, FireFox®, or other suitable browser. The nonvolatile memory can comprise flash memory, a harddrive, or other suitable memory device, and can have a size of at least 64 MB. The operating system and browser can be executed by the processor 200 by utilizing and accessing volatile memory 2020, which can comprise RAM memory having a size of at least 128 MB. Microprocessor can comprise a variety of general purpose industrial processors, such as for example i.MX series processors available from FreeScale Semiconductor, Inc. and can have an operating speed of at least about 300 MHz. Such processors may have integrated CAN communication capability and interfaces, if CAN electronics are used on the bed. However, a separate CAN interface can be utilized if the processor does not have integrated CAN capability.

Microprocessor 200 communicates with and drives the graphical user interfaces 50, 52 via display interfaces 209. Such interfaces 209 can comprise low voltage differential signaling transmitters and i2c buffer circuits, and/or other appropriate driver or interface circuitry for driving displays.

Additionally, in the example of FIG. 4, microprocessor 200 drives a speaker amplifier 205 to permit audio through a speaker 201. Microprocessor 200 also receives audio input from a microphone 211 via a microphone amplifier 203. Accordingly, alarms, music, nature sounds and other sounds can be driven by microprocessor 200 through speaker 201 and/or user interfaces 50/52. Additionally, audio input can be picked up via microphone 211 and stored via processor 200.

In this example, microprocessor 200 includes an integrated Ethernet interface. Accordingly, the microprocessor 200 can automatically provide output data for communication to a network in an Ethernet format. The format includes frames having a header, data section, and footer. The header contains the Media Access Control (MAC) addresses of both the sender and intended network recipient. Through its Ethernet communication circuitry, microprocessor 200 first performs a check on whether the connection is available to transmit. If a collision is detected (another device on the network has sent an Ethernet frame at the same time), then processor 200 will retransmit the frame after waiting a random time period up to a maximum time period. While the processor 200 has built-in Ethernet communication output in this example, a separate circuit or card could be used for this purpose.

The example of FIG. 4 further shows that the electronics system 110 of the patient support includes a WiFi interface 208. This interface 208 allows the processor 200 to communicate to the server 111 (and/or to other equipment) via a wireless local area network communication protocol, such as the IEEE 802.11 protocol. The wireless connection can utilize spread spectrum and/or frequency division multiplexing and can operate at a frequency of at least 900 MHz, such as 1 GHz and higher for example. For example, the wireless connection could be about 2.4 GHz.

As also shown in the example of FIG. 4, the processor 200 and many of the other components of the electronic system 110 are electrically isolated from the server 111 by way of isolator 210. Isolator 210 can provide electrical isolation via inductive, capacitive, and/or optical isolation circuitry. The isolator 210 provides at least 4.6 mm creepage distance, 2.5 mm of air clearance, and 1500 volts dielectric breakdown voltage. (Air clearance is the shortest distance through the air between two conductive elements. Creepage distance is the shortest distance on the surface of the insulating material between two conductive elements.) In another embodiment the isolation capability of isolator 210 provides at least 8.0 mm creepage distance, 2.5 mm of air clearance, and 5000 volts dielectric breakdown voltage. In another embodiment, the isolator 210 has at least 2.5 mm creepage distance and at least 2.0 mm air clearance, such as at least 4.0 mm creepage and 2.5 mm air clearance for example.

Connected to the isolator 210 is an Ethernet interface 212 which provides any necessary conversion of the isolator's signal into Ethernet protocol (such as that described above). For example, if the isolator provides a serial signal, the interface 212 can be a serial to Ethernet converter that converts or processes the serial signal to produce the desired Ethernet format (and vice versa). Connected to the interface 212 are Ethernet magnetics 214, which provide electric isolation, distortion removal and EMI suppression. The signal is then provided as an Ethernet signal at an Ethernet jack or connector 216, is hardwired to the server 111.

Figure 5:
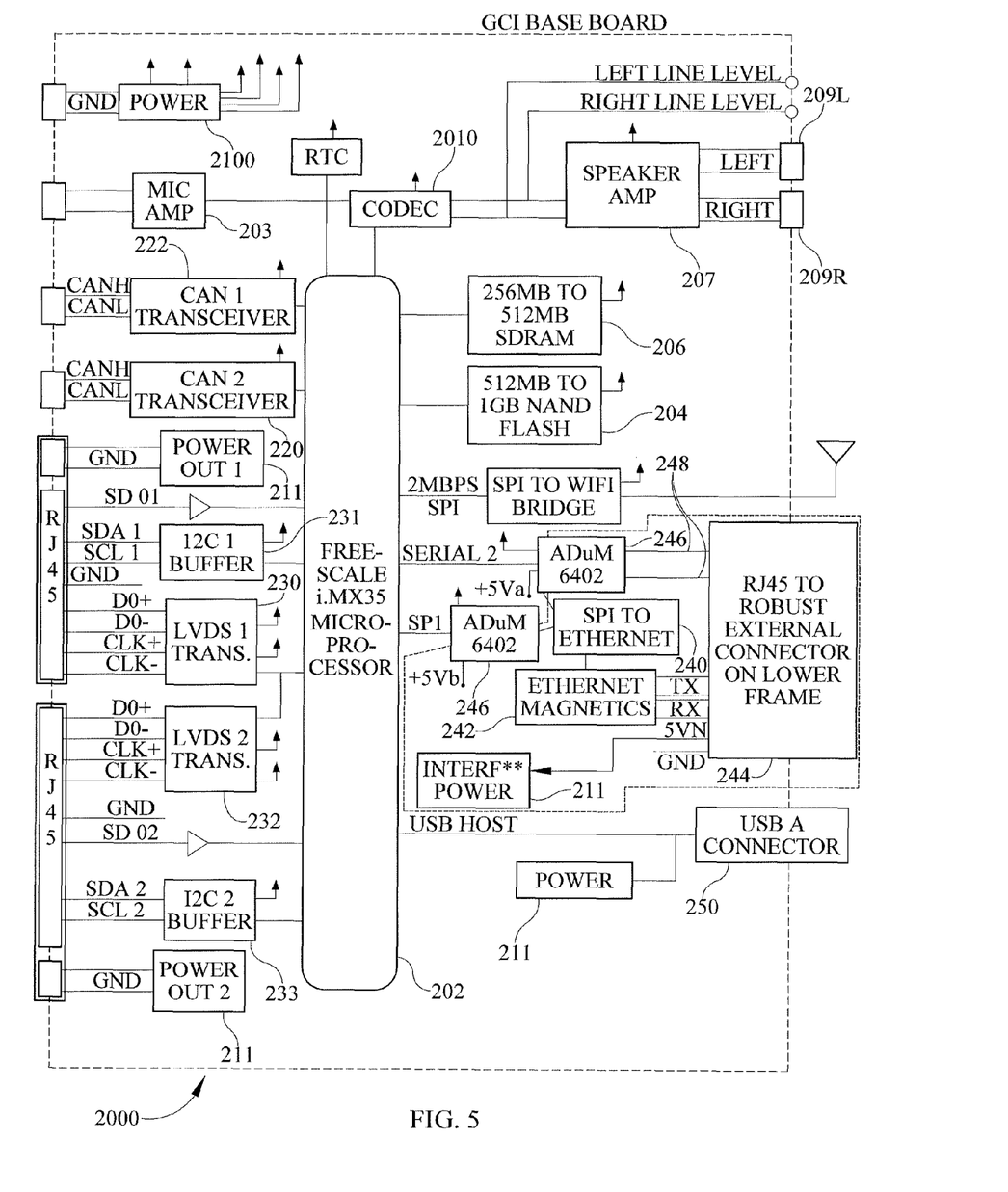
FIG. 5 is a block diagram of another embodiment of an electronic system of a patient support, configured in accordance with one or more principles of the present disclosure.

FIG. 5 is a block diagram of an illustrative embodiment of an electronics control system 2000 for a patient support. In this example, a microprocessor 202 runs an operating system storage on nonvolatile ROM memory 204 using volatile RAM memory 206. The operating system may comprise a general purpose, off-the shelf operating system not designed specifically for patient supports, such as a Windows® operating system from Microsoft, for example. The ROM memory 204 may also include browser software. The operating system and/or browser can allow the system 2000 to act as a client to a remote server when communicating with such server. A Codec device 2010 converts a digital data stream from the microprocessor 202 into an analog signal for use by a speaker amplifier 207 which drives speakers 209R and 209L. Accordingly, audio, such as music and alarms can be provided from the processor 202. Additionally, the Codec device 2010 converts analog signals generated by a microphone 211 (and amplified by a microphone amplifier 203) into digital signals for use by the processor 202.

The microprocessor 202 controls patient support functions through interfaces to patient support actuator electronics, runs graphical user interface functions through interfaces to user interfaces, communicates with a remote network through one or more network interfaces, and drives a removable storage device. More details on the various circuits of this illustrative embodiment that allow such functions are provided in the following description.

Two CAN interfaces 220 and 222 (e.g., transceivers) are provided in this illustrative embodiment, and these provide connectivity to a patient support actuator control electronics. These transceivers 220, 222 provide commands from the microprocessor to the CAN network, or other device network, which then control the actuators (e.g., pumps, motors, linear actuators, blowers, sensors, etc) that allow the patient support to move, provide therapy, protect, and/or sense. Some examples of such actuators are described with respect to the example of FIGS. 1-4, although many others are possible.

Display driver circuits 230, 231, 232, and 233 are provided and drive graphical user interfaces, such as touchscreens, LCD's and other displays. In this example, an LVDS circuit 230 and an I2C buffer 231 drive a first GUI, and LVDS circuit 232 and I2C buffer 233 drive a second GUI.

A network interface circuit is also provided. The interface circuit interfaces with a remote network computer (remote from the patient's room). In this example, the network interface comprises a serial to Ethernet converter 240 which converts serial signals from the processor 202 into Ethernet signals. For example, converter 240 could comprise an Ethernet interface board or chip. In another example, processor 202 comprises a processor with built-in Ethernet communication capability. The output of the converter 240 is provided to Ethernet magnetics 242 which then provides the Ethernet signal to jack or connector 244. In this example, the connector 244 is an RJ45 Ethernet jack. An Ethernet cable can then be connected from the network to the connector 244 to allow for communications with the patient support electronics 2000.

Electric isolators 246 provide electrical isolation of the electronics 2000 from the network. In this example, the isolators 246 operate on digital signals and therefore are digital isolators. The isolators 246 provide such isolation via inductance by using microtransformers that can convert digital signals at high speed. The isolator 210 has at least 4 mm creepage distance and 2.4 mm of air clearance, and can isolate at least up to 240 volts AC in one embodiment. In another embodiment, the isolator 210 has greater than 2.0 mm creepage distance and greater than 2.0 mm of air clearance. In another embodiment, the isolator 210 has at least 2.5 mm creepage distance and at least 2.5 mm air clearance. In yet another embodiment, the isolator 210 has a creepage distance and air clearance greater than that of Ethernet magnetics 242.

An identifier of the room in which the patient support is located is also provided to the processor 202 via lines 248. These lines are isolated via the isolator 246. The room identification may come from a wall unit at the network connection and may be carried by the same cable that carries the network signal to the connector 244. Alternatively, the room ID may be provided via different communication paths. The processor 202 may then transfer the room identifier back to the network via the connector 244. The signal may be provided in the network communication packet, or over a separate dedicated line (such as transmit line 248TX)

A USB connector (e.g., outlet, port, or jack) is provided in this example, as shown at 250. The USB connector 250 allows data to be stored by the processor 202 on a portable removable card or memory device or stick, and also to be transferred from the card or device or stick to the processor 202 for use by the processor 202. Such data may include patient data, patient support data, multimedia data, audio data, video data, email data, document data, or other data or information useful to the caregiver, hospital, or patient. The USB connector 250 can be used to upgrade or modify the programs and operating system in memory 204. The connector 250 can also be used to connect the patient support to other medical devices such as pumps, ventilators, or monitors, or to other consumer electronics devices, such as phones, cameras, PDA's, personal computers, MP3 players, electronic book devices, and the like.

Power to the circuit 2000 can be provided by power converter 2100 which can provide various power levels needed as appropriate. This power can also be passed on to other devices, such as via power outputs 2110.

Of course many other embodiments still utilizing the inventive principles herein are possible. For example, while multiple clock lines are provided in the example of FIG. 5, a clock signal can be provided along with data over an integrated data/clock line.

Figure 6:
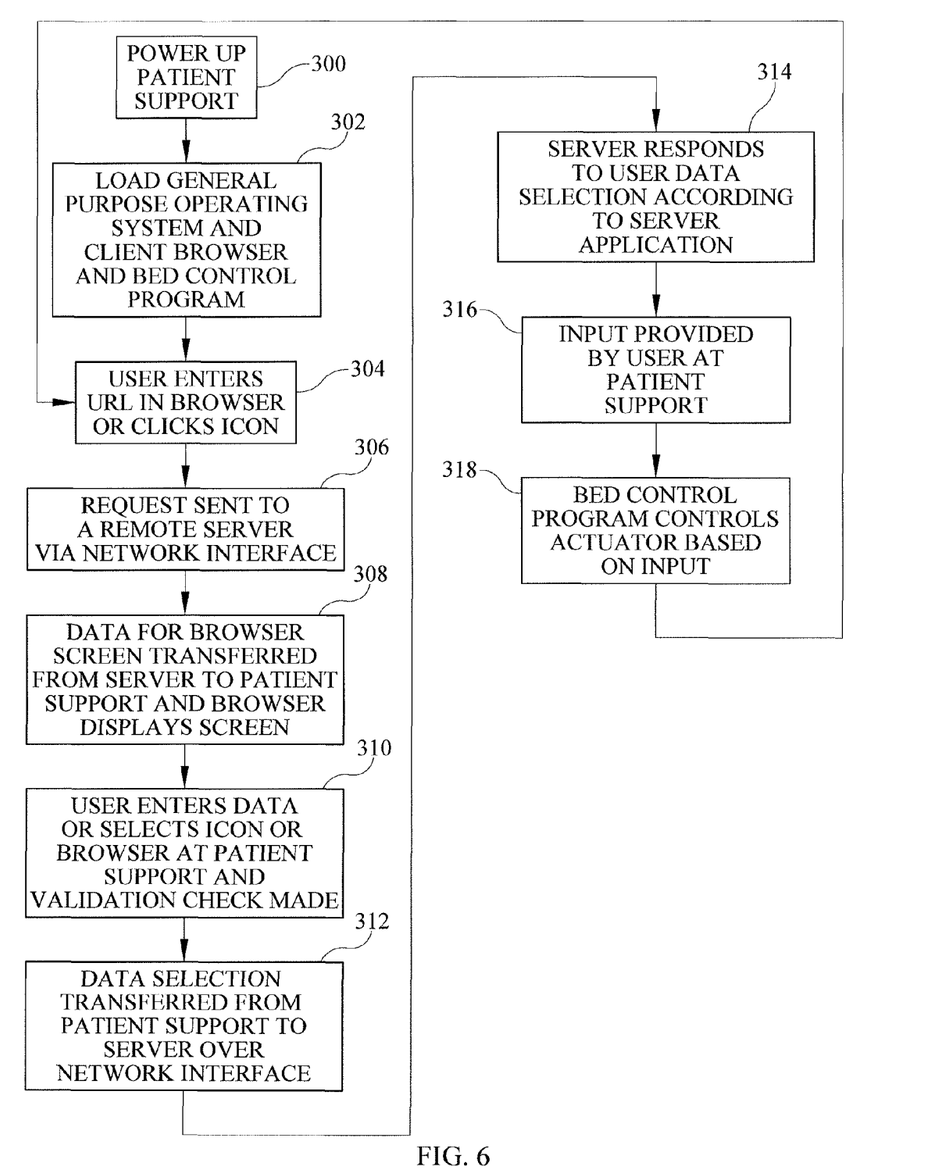
FIG. 6 is a flow diagram of a method for communication between an electronics system of a patient support and a remote server, according to one or more principles of the present disclosure.

FIG. 6 is a flow diagram of an illustrative method for communication between an electronics system of a patient support and a remote server, according to one or more principles of the present disclosure. According to this method, the patient support is powered, as shown at operation 300. The general purpose operating system and client browser program and bed control program are then loaded into memory on the patient support, as shown at operation 302. A user of the patient support enters a url or otherwise indicates the desired service, such as by clicking a link or icon, as shown at operation 304. A touchscreen or other suitable display and input device can be used for this purpose. A request is sent to a remote servicer via a network interface to launch the desired remote application or access the desired remote page, as shown at block 306.

At block 308, data is transferred from the remote server to the patient support and the browser software on the patient support displays the screen as instructed by the data from the server. The user enters data or selects an icon or location on the screen displayed on the patient support, as shown at operation 310. Data representing the selection is again transferred from the patient support to the server over the network interface, as shown at operation 312. The network interface could include one or more of the interfaces described above, such as isolator 246, magnetics 242, connector 244, converter 240, and/or Spi to WiFi bridge 249, or other suitable interface.

As shown at block 314, the server responds to the user data selection according to the code/program on the server for the selected application. Input is again provided by user at the patient support as shown at block 316. Such input can be a command to the patient support apparatus to raise or lower or tilt or inflate or provide therapy, and can be provided via a button or touchscreen. The bed control program responds to this input and controls the appropriate actuator to achieve the desired patient support function, as shown at operation 318. The process is iterative, such that additional commands regarding operation of remote applications from the remote server, and additional commands for control of the patient support can be provided, at any time that the patient support is running.

Figure 7:
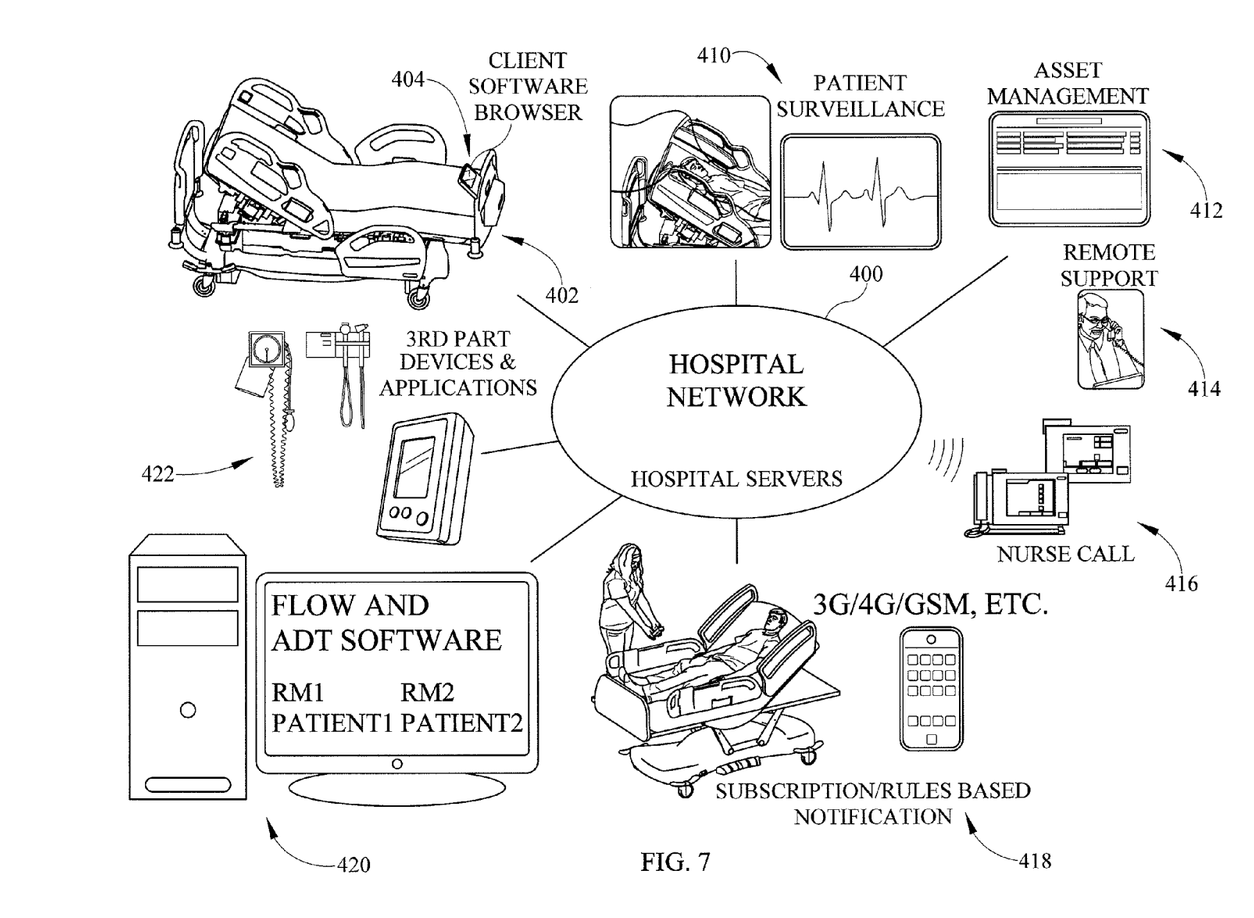
FIG. 7 is a schematic diagram of an embodiment of a hospital network with a server and a client patient support apparatus, configured in accordance with one or more principles of the present disclosure.

FIG. 7 is a schematic diagram of an illustrative embodiment of hospital network with server and client patient support apparatus, configured in accordance with one or more principles of the present disclosure. In this embodiment, a patient support with a client software browser 404 is connected via a hospital network 400 having servers. The network 400 is further connected to various third party medical devices, such as monitors or pumps, and third party applications, such as general computing applications, as shown at 422. Additionally, the network 400 is connected to software that keeps track of patient and/or caregiver tasks and locations in the hospital, as shown at 420, such as which patients are in which rooms. Such software could comprise admission, discharge, transfer (ADT) software. Moreover, caregivers can be provided with portable messaging or alerting devices 418 which are also in communication with the servers, as shown at 418. Such devices could comprise badges, pagers, telephones, or other communication devices.

A nurse call system 416 can also connect with the network 400. Additionally, data regarding patient surveillance, such as patient vital signs data can be communicated to the network 400 via the patient support 404 or directly. Moreover, asset management software 412 can be used to track hospital equipment and can run on one or more computers or servers connected to the network 400. Also, communications regarding support and diagnostics can be delivered via the network 400. Accordingly, many pieces of software and hardware can communicate through the network 400. The network 400 may utilize Internet and/or Ethernet protocols to provide such communications.

Figure 8:
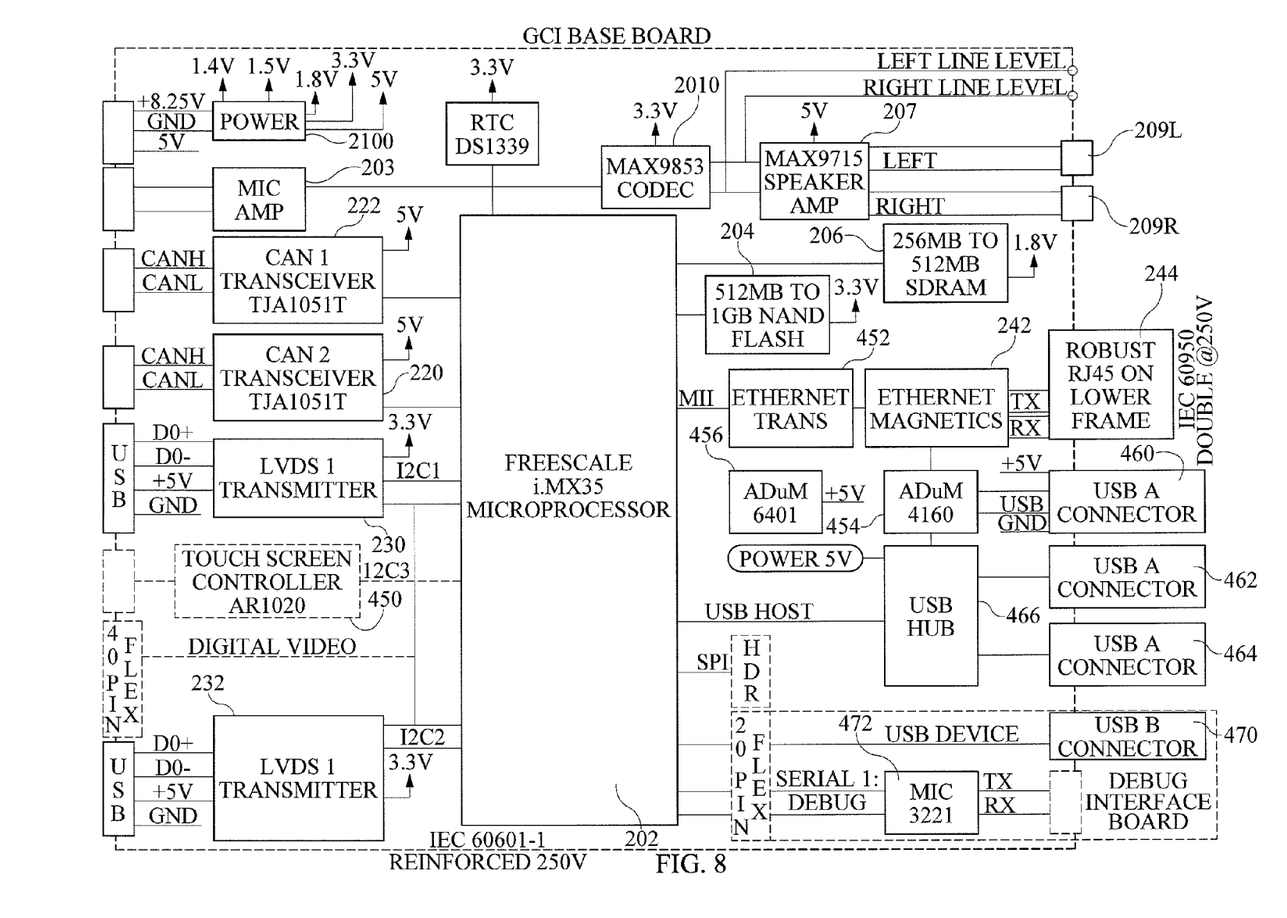
FIG. 8 is block diagram of yet another embodiment of an electronic system of a patient support, configured in accordance with one or more principles of the present disclosure.

FIG. 8 is block diagram of yet another illustrative embodiment of an electronic system of a patient support, configured in accordance with one or more principles of the present disclosure. This embodiment is similar to the embodiment of FIG. 5. Accordingly, much of the description above regarding FIG. 5 applies with respect to the embodiment of FIG. 8 and will not be repeated here, except for salient differences. In particular, the display drivers 230 and 232 do not include clock lines, because the clock signal is provided over the data lines (DO+ and DO−) in this embodiment. Also, in this embodiment, a touchscreen controller interface 450 is provided, to allow the circuit to connect with an external touchscreen (e.g., in the event that the hospital bed does not include a graphical display, a retrofit touchscreen can be provided and can interface to the circuitry through interface 450).

As another difference, in this example, an Ethernet isolator chip 452 is provided which electrically isolates the Ethernet signal coming from the connector 244 through the Ethernet magnetics 242 to the processor 202 (and vice versa). Such chip could comprise a 10/100/ and/or 1000 MBit isolation module, such as available through Halo Electronics, CoilCraft Inc and the like, and can provide isolation in accordance with IEC60601-1 specifications, for example. In this embodiment, a USB connector 460 is provided for use by the caregiver and/or patient. A USB isolation chip 454 is provided and performs electrical isolation of the USB signal that the patient/caregiver accesses. Here, the isolation provided by the isolators 452 and 454 provides at least 2.5 mm creepage distance and at least 2.0 mm air clearance, such as at least 4.6 mm creepage and 2.5 mm air clearance for example. The USB signal is provided to/from the processor 202 via a USB hub 466. In this example, the hub 466 communicates with the isolator 454 which provides the signal at the connector 460. However, additional non-isolated USB connectors 462 and 464 are also provided, and allow for USB access to the processor 202 by service technicians, and others besides the end user. Additional communication ports (USB port 470 and RS232 port 472) are provided for programming, updates, service and the like.

The foregoing description of various embodiments and principles of the disclosure have been presented for the purposes of illustration and description. It is not intended to be exhaustive or to limit the disclosure to the precise forms disclosed. Many alternatives, modifications and variations will be apparent to those skilled in the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and broad scope of the inventions defined by the claims.

The invention claimed is:

1. A person support apparatus, comprising
a frame configured to support a person,
an actuator operable to impart movement to at least a portion of the frame, and
an electronics system coupled to the person support apparatus and configured to control the movable actuator, wherein the electronics system comprises a processor, a memory, a user interface configured to display information as directed by the processor, a network connector configured to connect to a hospital network via hardwired connection, a network interface, wherein the network interface is configured to allow for data communication with a hospital network via the network connector, a general purpose operating system executable by the processor, wherein the general purpose operating system is configured to run a plurality of computer software applications not designed for person support apparatuses, browser software executable by the processor and configured to allow the electronics to act as a client computer by sending a request to a remote server to perform a task, receiving data defining a screen to be displayed on the user interface in response to the request, receiving input from a user at a portion of the screen, and sending the input to the remote server, control software configured to control the movable actuator through at least one input from a user, and an electrical isolator configured to provide electrical isolation of the network connector from at least a portion of the electronics system.

2. The apparatus as recited in claim 1, wherein the electrical isolator has at least one of an air clearance distance and a creepage distance of greater than 2.0 mm.

3. The apparatus as recited in claim 1, wherein the electrical isolator is configured to provide isolation through at least one of optical, inductive, magnetic, and capacitive coupling.

4. The apparatus as recited in claim 1, wherein the isolator comprises a digital isolator.

5. The apparatus as recited in claim 1, further comprising a converter circuit configured to convert a network signal to a signal corresponding to the protocol of output on the processor.

6. The apparatus as recited in claim 5 wherein the isolator is in communication with the converter circuit.

7. The apparatus as recited in claim 1, wherein the electronics system includes a magnetic interface configured to provide signals to and from the network connector.

8. The apparatus as recited in claim 1, wherein the electronics system is configured to receive an identification of the room in which the patient support is located and to send the identification via the network connector.

9. The apparatus as recited in claim 1, wherein the electronics system is configured to cause a location identification signal to be communicated to the remote server, such that the remote server can associate the data from the electronics system to a physical location in a hospital.

10. The apparatus as recited in claim 1, wherein the processor includes a built-in network communication circuit.

11. The apparatus as recited in claim 10, wherein the network communication circuit comprises an Ethernet communication circuit.

12. The apparatus as recited in claim 1, wherein the browser software and the control software are executed by the processor.

13. The apparatus as recited in claim 1, wherein the processor communicates with a controller executing the control software.

14. The apparatus as recite in claim 13, wherein the controller comprises a controller area network (CAN) module.

15. The apparatus as recited in claim 1, wherein the processor includes at least two of an integrated Ethernet interface, an integrated CAN interface, an integrated image processing unit, and a USB interface.

16. The apparatus as recited in claim 1, further comprising at least one USB port provided on the person support apparatus and coupled to the electronics system.

* * * * *